United States Patent [19]

Chamberlain

[11] Patent Number: 5,099,049

[45] Date of Patent: Mar. 24, 1992

[54] CHELATE COMPOSITIONS AND THEIR PRODUCTION

[75] Inventor: Peter Chamberlain, West Yorkshire, England

[73] Assignee: Allied Colloids Limited, United Kingdom

[21] Appl. No.: 673,596

[22] Filed: Mar. 22, 1991

[30] Foreign Application Priority Data

Mar. 23, 1990 [GB] United Kingdom ............... 9006606

[51] Int. Cl.$^5$ ............................................. C07F 15/02
[52] U.S. Cl. ......................................... 556/148; 556/147; 71/DIG. 2; 71/27; 71/28; 71/97
[58] Field of Search ..................... 556/138, 147, 148; 71/DIG. 2, 97, 27, 28, 29, 30

[56] References Cited

U.S. PATENT DOCUMENTS

| | | | |
|---|---|---|---|
| 4,687,658 | 8/1987 | Quay | 556/147 X |
| 4,687,659 | 8/1987 | Quay | 556/148 X |
| 4,714,607 | 12/1987 | Klaveness | 556/148 X |
| 4,965,211 | 10/1990 | Wieder et al. | 556/148 X |

*Primary Examiner*—Arthur C. Prescott
*Attorney, Agent, or Firm*—Ostrolenk, Faber, Gerb & Soffen

[57] ABSTRACT

A compound that is the water insoluble hydrochloride addition salt of the dihydrogen ferric complex of diethylene triamine penta-acetic acid, DTPAH$_5$, namely DTPAFeH$_3$Cl, which has been made in pure form from DTPANa$_5$, and which can be used in an agricultural nutrient composition.

12 Claims, No Drawings

CHELATE COMPOSITIONS AND THEIR PRODUCTION

This invention relates to a novel diethylene triamine penta acetate compound, agricultural compositions containing this compound, and the use of this compound as an intermediate for the production of other diethylene triamine penta acetate compounds.

Diethylene triamine penta acetate (DTPA) compounds have the formula

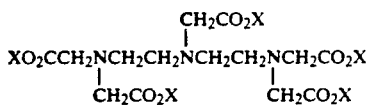

wherein each X is a hydrogen atom or a cation. When all the carboxylic groups are in the form of free acid, the formula can be abbreviated as $DTPAH_5$. When all the carboxylic groups are in the form of sodium carboxylates, the formula can be written as $DTPANa_5$. When three of the groups are complexed with ferric iron the formula can be written as, for instance, $DTPAFeNa_2$ (when the two carboxylics that are not complexed with ferric are in the sodium form).

Ferric complexes of DTPA such as this disodium complex, and the corresponding monosodium monohydrogen and diammonium complexes, are commercially very useful as a source of soluble iron in horticultural and other agricultural nutrient compositions. A problem that arises with such compositions is that they tend to contain rather large amounts of unwanted inert by-products (with the result that the active iron content in the composition is, on a weight basis, lower than is desirable) and unwanted trace impurities that may be considered unacceptable for some uses.

The pentasodium compound $DTPANa_5$ in practice is conveniently made by reaction of diethylene triamine with sodium cyanide, formaldehyde and water. Impurities that may be present in it include small amounts of nitrilo-triacetic acid (NTA), trace amounts of sodium cyanide, and possibly other impurities. The product is generally used in the form of an aqueous solution.

The iron chelate $DTPAFeNa_2$ is made most conveniently by reaction of ferric chloride or ferric sulphate with the pentasodium form, namely $DTPANa_5$. This produces a solution of 1 mole $DTPAFeNa_2$ mixed with three moles of sodium chloride or 1.5 moles of sodium sulphate. Reaction with sulphuric acid converts it to $DTPAFeNaH$, with a mole of sodium bisulphate as additional by-product.

However, separation is difficult since the iron chelate and salts are both water-soluble. Commercially, it is therefore usual to convert the aqueous mixture of the mixture of chelate and excess salt directly to solid, by, for example, spray drying. The final product is thus diluted with a large amount of inert by-product. Additionally, any impurities in the starting pentasodium compound will have been carried through into the end product and, because of the difficulty of purifying the end product, will remain in that. This is particularly a problem with the presence of nitrilo triacetic acid (NTA), as it has been alleged to be toxic to humans.

In theory, an iron complex could be made by reaction between ferric hydroxide and relatively pure free acid $DTPAH_5$. Unfortunately, although powdered $DTPAH_5$ is commercially available it is expensive and its use still leads to impure products, and ferric hydroxide is a gelatinous material which readily converts to unreactive forms.

It would be desirable to be able to provide, from readily available starting materials, a ferric complex of DTPA that can be purified to remove these starting impurities and the inert by-products.

According to the invention, I provide a compound that is the water insoluble hydrochloride addition salt of the dihydrogen ferric complex of diethylene triamine penta acetic acid, $DTPAH_5$.

This particular compound, namely $DTPAFeH_3Cl$, has the advantage that it is readily made from readily available starting materials (that can be impure) and yet has physical properties that make its separation and purification very easy. So far as I am aware no other DTPA compound possesses this desirable combination of economic availability and suitable physical properties. For instance $DTPAFeH_2$ is insoluble but the physical state of it, when it is in the solid form is such that it cannot easily be separated from the aqueous medium in which it is formed, and thus it is difficult to purify.

The defined hydrogen chloride acid addition salt, $DTPAFeH_3Cl$, has very low solubility both in strong acid and in water. It can be separated from the mother liquors containing sodium chloride or other by-products and impurities and can be washed repeatedly with water to remove such impurities and by-products, so as to give a substantially pure form of the acid addition salt.

One way of making $DTPAFeH_3Cl$ is by adding sufficient hydrochloric acid to an aqueous solution of a water-soluble compound $DTPAFeX_2$ (where X can be the same or different and are hydrogen atoms or cations, usually monovalent, such as sodium or other alkali metal or ammonium) to cause precipitation of $DTPAFeH_3Cl$. For instance the starting material can have both groups X as sodium, both as ammonium, or one as hydrogen and the other as sodium or ammonium.

This method can conveniently be applied to the purification of $DTPAFeH_3Cl$. Thus the salt can be separated from the liquid in which it is formed, optionally washed, and then dissolved in alkali to form the soluble compound $DTPAFeX_2$, this solution can be filtered, and the salt precipitated by adding hydrochloric acid.

The starting compound for this process can be made from $DTPANa_5$, and so a preferred process according to the invention for making the novel salt from conveniently available materials involves mixing $DTPAHa_5$ (in the form of an aqueous solution) with a substantially equimolar amount of ferric chloride (preferably as a solid, in powder or lump form) to form a solution containing $DTPAFeNa_2$ and sodium chloride. This mixing may be conducted in the presence of concentrated hydrochloric acid, generally in an amount of less than 2 moles per mole of $DTPANa_5$.

Preferably the pH of the mixture is such that $DTPAFeX_2$ is formed as a solution. In order to obtain the insoluble $DTPAFeH_3Cl$ from solutions of $DTPAFeX_2$, for instance the disodium compound as obtain above, it is necessary to render the solution highly acidic by the addition of hydrochloric acid. Generally the pH must be below 2, generally below 1.5 and prefereably about 1 or less, e.g., down to 0.5.

The salt is separated from the mother liquor by filtration of centrifugation, and then washed free of sodium chloride.

The pentasodium compound that is used as the starting material can be impure, and the process can give DTPAFeH₃Cl in pure form. However the process does involve the use of concentrated hydrochloric acid, and the invention includes also a process in which this can be avoided. The invention includes mixing DTPAH₅ with DTPANa₅ and ferric chloride in warm aqueous solution. Generally the process is conducted by mixing solid DTPAH₅ with an aqueous solution of DTPAHa₅, warming this mixture to a temperature typically in the range 50° to 80° C. and then adding ferric chloride generally in powder or lump form. On cooling, the desired salt precipitates out from the solution. The molar ratio of DTPAH₅:DTPANa₅ is preferably in the range about 1:1–2:1, most preferably it is about 1:5:1.

The invention includes the use of purified DTPA-FeH₃Cl as an intermediate for the production of other DTPAFeX₂ compounds by reaction in aqueous alkali, and it also includes the resultant compounds made in this way. These compounds are contaminated with less by-products (such as Na₂SO₄ and/or NaHSO₄ and for NaCl) and less impurities (such as NTA) than existing commercial forms of such compounds. Thus DTPA-FeH₃Cl can be reacted with aqueous ammonium hydroxide to form DTPAFe(NH₄)₂ contaminated with only one mole of ammonium chloride, and this solution can conveniently have a concentration of about 6% iron. Similarly, when DTPAFeH₃Cl is reacted with 2 moles sodium hydroxide, the compound DTPAFeNaH is formed, together with only one mole of sodium chloride. Drying the reaction mixture gives a product containing about 10% Fe.

DTPAFeH₃Cl is too strongly acid to be solubilised and used agriculturally by itself, but is satisfactory for agricultural use and is solubilised when mixed with a buffer in water.

Accordingly the invention also includes solid, agricultural nutrient compositions comprising DTPA-FeH₃Cl and a buffer, and optionally an inert carrier. The amount of buffer must be sufficient to solubilise the compound when the composition is exposed to water, and generally to convert it to a soluble salt, for example, DTPAFe(NH₄)₂. The ammonium compounds and the phosphate compounds conventionally present in any fertiliser compositions will act as buffers and so compositions according to the invention comprise blends of DTPAFeH₃Cl with ammonium and/or phosphate fertiliser components.

Typical components include ammonium sulphate, ammonium nitrate, mono-ammonium phosphate, diammonium phosphate, potassium nitrate and urea.

Such a mix may be dissolved in water to give a clear solution which may be used subsequently as a fertiliser, by spraying on to the plant or by incorporation into the growing medium.

The following are examples of the invention:

EXAMPLE 1

Preparation of DTPAFeH₃Cl from DTPANa₅

To 1310 g of a 39% solution (1 mole) of substantially pure, commercial grade, DTPANa₅ was added water (250 g) and 35% hydrochloric acid (175 g).

The solution was warmed to 70° C. and lumps of ferric chloride hexahydrate (279 g, 1 mole) were added slowly.

When reaction was complete, more hydrochloric acid was added to pH 1 (approx. 175 g 35% acid was required).

On cooling, yellow crystals of the addition salt, DTPAFeH₃Cl, separated out. Vacuum filtration followed by washing with water and drying gave 460 g of the hydrochloride. The iron content was 11.3% (93% recovery of iron).

A small sample of the product was purified by dissolving it in 20% aqueous ammonia, precipitated by addition of hydrochloric acid to pH 1, and recovered by filtration.

|  | FOUND | CALCULATED |
|---|---|---|
| Iron (%) | 11.6 | 11.6 |
| Nitrogen (%) | 8.6 | 8.7 |
| Chloride (%) | 7.6 | 7.4 |
| Equivalent Weight | 160.9 (pH titration) | 160.8 (for tribasic acid) |

The NTA level was less than 0.1%.

EXAMPLE 2

This was identical to Example 1, except that the pH was lowered to pH 0.8.

The recovery of iron was 84%.

EXAMPLE 3

This was identical to Example 1, except that the pH was lowered to pH 1.5.

The recovery of iron was 73%.

EXAMPLE 4

This was identical to Example except that the DTPANa₅ contained 3% nitrilo-triacetic acid (NTA).

Analysis of the crystalline DTPAFeH₃Cl showed an NTA content of less than 0.1%.

EXAMPLE 5

Preparation of DTPAFeH₃Cl from DTPANa₅ and DTPAH₅

To 1310 g of a 39% solution (1 mole) of DTPANa₅ in water (2700 g) was added 601.5 g (1.5 mole) of 98% pure DTPAH₅. The stirred mix was heated to 70° C. When the acid had dissolved, lumps of ferric chloride hexahydrate (698 g, 2.5 mole) were added. The temperature was maintained at 70° C. until reaction was complete.

On cooling, DTPAFeH₃Cl separated out. The mother liquor had pH 1.

The product, after filtration, washing and drying, had an iron content of 11.3% (85% recovery of iron).

EXAMPLE 6

Preparation of DTPAFeNH₄)₂

To 20% aqueous ammonia (112 g) and water (105 g) was added gradually, with stirring DTPAFeH₃Cl (250 g).

The final deep red solution of DTPAFe(NH₄)₂ and ammonium chloride had an iron content of 6.2% w/w and pH 7.

EXAMPLE 7

Preparation of an Iron-Containing Soluble Fertiliser

To 100 g of a 30-10-10 (N-P-K) soluble fertiliser made from urea, diammonium phosphate and potassium nitrate was dry blended 2 g of $DTPAFeH_3Cl$.

The resulting material was totally soluble in water to give a soluble iron-containing N-P-K fertiliser.

I claim:

1. A compound that is the water insoluble hydrochloride addition salt of the dihydrogen ferric complex of diethylene triamine penta-acetic acid, $DTPAH_5$.

2. A method of making the salt according to claim 1 wherein hydrochloric acid is reacted with an aqueous solution of the compound $DTPAFeX_2$ wherein X are the same or different and each is hydrogen, or a monovalent cation, in an amount sufficient to cause a precipitate of the said salt to form, and the precipitate is then recovered.

3. A method according to claim 2 in which the precipitate is recovered by separating by filtration, dissolving the precipitate in alkali, filtering the resultant solution, re-precipitating the salt by the addition of hydrochloric acid to the filtrate, and collecting the resultant precipitate by filtration.

4. A method according to claim 2 comprising the preliminary steps of mixing $DTPANa_5$ with ferric chloride in the presence of sufficient concentrated hydrochloric acid to reduce the reaction pH to below 2, and preferably to 1 or less.

5. A method of making a salt according to claim 1 comprising mixing $DTPAH_5$ with $DTPANa_5$ and ferric chloride in aqueous solution at an elevated temperature at which the said salt substantially remains in solution, cooling the solution and thereby precipitating the said salt, and recovering the precipitated salt.

6. A method according to claim 5 wherein the molar ratio of $DTPAH_5$: $DTPANa_5$ is in the range 1:1-2:1, preferably 1.5:1, and the process is conducted by mixing solid $DTPAH_5$ with an aqueous solution of $DTPANa_5$, warming the mixture to 50° to 80° C. and adding ferric chloride.

7. A compound $DTPAFeX_2$ wherein X are the same or different and each is hydrogen, or monovalent cation, and which has been made by reaction of a salt according to claim 1 with aqueous alkali.

8. An agricultural nutrient composition comprising a salt according to claim 1 and a buffer that will solubilise the said salt in water.

9. A composition according to claim 8 wherein the buffer is selected from ammonium compounds and phosphate compounds.

10. A composition according to claim 9 wherein the buffer is selected from the group consisting of ammonium sulphate, ammonium nitrate, mono-ammonium phosphate, diammonium phosphate, potassium nitrate and urea.

11. A method according to claim 4 in which the concentrated hydrochloric acid is sufficient to reduce the reaction pH to 1 or less.

12. A method according to claim 5 wherein the molar ratio of $DTPAH_5$:$DTPANa_5$ is 1:5:1.

* * * * *